(12) United States Patent
Ho

(10) Patent No.: US 8,980,245 B2
(45) Date of Patent: *Mar. 17, 2015

(54) PEG-INTERFERON λ1 CONJUGATES AND METHODS OF TREATING VIRAL INFECTIONS

(71) Applicant: Nanogen Pharmaceutical Biotechnology, Ho Chi Minh (VN)

(72) Inventor: Nhan Ho, Ho Chi Minh (VN)

(73) Assignee: Nanogen Pharmaceutical Biotechnology, Ho Chi Minh (VN)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,253

(22) Filed: May 1, 2013

(65) Prior Publication Data

US 2013/0230490 A1      Sep. 5, 2013

Related U.S. Application Data

(63) Continuation of application No. 13/409,946, filed on Mar. 1, 2012, now Pat. No. 8,454,947.

(51) Int. Cl.
| | | |
|---|---|---|
| *A61K 38/21* | (2006.01) | |
| *C07K 14/555* | (2006.01) | |
| *A61K 47/48* | (2006.01) | |
| *A61K 38/00* | (2006.01) | |

(52) U.S. Cl.
CPC ........... *A61K 47/48215* (2013.01); *A61K 38/21* (2013.01); *C07K 14/555* (2013.01); *A61K 38/00* (2013.01)
USPC ......................................... 424/85.4; 530/351

(58) Field of Classification Search
None
See application file for complete search history.

(56) References Cited

U.S. PATENT DOCUMENTS

| | | |
|---|---|---|
| 5,382,657 A | 1/1995 | Karasiewicz et al. |
| 2008/0096252 A1 | 4/2008 | Zamost et al. |
| 2008/0132681 A1 | 6/2008 | Hayes et al. |
| 2010/0003722 A1 | 1/2010 | Zamost et al. |

FOREIGN PATENT DOCUMENTS

WO    WO/2009/149377    10/2009

*Primary Examiner* — Robert Landsman
*Assistant Examiner* — Bruce D Hissong
(74) *Attorney, Agent, or Firm* — Sam L. Nguyen; Hamilton, DeSanctis & Cha, LLP

(57) ABSTRACT

The present application discloses new PEG-interferon lambda 1 conjugates (PEG-IFNλ1), processes for their preparation, pharmaceutical compositions containing these conjugates and processes for making the same. These conjugates have increased blood half-lives and persistence time compared to IFNλ1 and are effective in the treatment of hepatitis B and hepatitis C.

15 Claims, 6 Drawing Sheets

SEQ ID 1:
ATGGGCCCTGTTCCGACCTCTAAACCTACCACCACGGGTAAGGGTTGTCATATTGGTC
GTTTCAAGTCTCTGTCCCCGCAGGAACTGGCCTCTTTCAAGAAAGCTCGTGATGCCCT
GGAAGAGTCTCTGAAGCTGAAAAACTGGAGCTGTTCTTCCCCGGTGTTCCCGGGCAAT
TGGGACCTGCGCCTGCTGCAGGTTCGCGAACGCCCGGTGGCTCTGGAAGCTGAGCTG
GCTCTGACCCTGAAAGTACTGGAAGCGGCGGCTGGTCCGGCCCTGGAAGACGTTCTG
GATCAGCCGCTGCACACCCTGCATCATATTCTGTCCCAGCTGCAGGCTTGCATCCAGC
CTCAGCCAACCGCCGGTCCGCGTCCACGTGGCCGTCTGCACCACTGGCTGCATCGCCT
GCAGGAAGCGCCGAAAAAGGAGAGCGCTGGCTGCCTGGAAGCAAGCGTAACCTTTA
ACCTGTTCCGTCTGCTGACTCGTGACCTGAAATATGTTGCAGATGGCAATCTGTGCCT
GCGTACCTCCACCCACCCGGAATCCACCTGA

*Figure 1*

SEQ ID 2:
Met G P V P T S K P T T T G K G C H I G R F K S L S P Q E L A S F K K A R D A L E E S L
K L K N W S C S S P V F P G N W D L R L L Q V R E R P V A L E A E L A L T L K V L E A
A A G P A L E D V L D Q P L H T L H H I L S Q L Q A C I Q P Q P T A G P R P R G R L H H
W L H R L Q E A P K K E S A G C L E A S V T F N L F R L L T R D L K Y V A D G N L C L
R T S T H P E S T

*Figure 2*

1: Vector pET26b(+)
2: Vector pET26b(+) digested by NdeL and HindIII
3: Vector PAPG110-IFN lambda digested by NdeI and HindIII
4: DNA massRuler pattern of Fermentas 1: Protein pattern of Fermentas
2: *E.coli*-pNanogen1-IL29 uninduced
3: *E.coli*-pNanogen1-LI29 induced by IPTG 1: Peginterferon lambda 1, lot PIL290050511
2: Protein pattern of MBI Fermentas
3: Interferon lambda 1, lot IL290030411

PEG-INTERFERON λ1 CONJUGATES AND METHODS OF TREATING VIRAL INFECTIONS

RELATED APPLICATION

The present application claims the benefit of U.S. Non-Provisional application Ser. No. 13/409,946, filed Mar. 1, 2012, which claims priority to Vietnamese Patent Application serial No. VN1-2011-02222, filed Aug. 25, 2011, both of which are incorporated herein by reference.

FIELD OF THE INVENTION

In one embodiment, the present application discloses pegylated derivatives of recombinant human interferon lambda 1 (PEG-interferon lambda 1 conjugates or PEG-IFNλ1), processes for their preparation, pharmaceutical compositions containing these conjugates and processes for making the same.

BACKGROUND OF THE INVENTION

Hepatitis C virus (HCV) is a major health problem and the leading cause of chronic liver disease throughout the world. It is estimated that at least 180 million people worldwide are chronically infected with HCV. In Vietnam, the proportion of infected HCV individuals in the population is 4-9%. Approximately 55-85% of acutely infected HCV individuals will convert to chronic infection, 5-25% of these chronic carriers are at risk of developing cirrhosis after 25-30 years and of those with cirrhosis, 30% are at risk of liver decompensation over 10 years, and 1-3% will develop liver cancer each year. According to epidemiological research, HCV is the cause of 40% of individuals in final stage cirrhosis and 60% in hepatoma.

Currently, α-interferons (AI) are the therapies of choice for the treatment of chronic HCV infection. AI can give a persistent response to HCV in approximately 70% of cases, however these interferons cause many side-effects, even in the case of PEG-interferon alpha. These side-effects can sometimes limit treatment, leaving the treatment of patients incomplete. Side-effects include influenza-like symptoms and hematologic effects such as thalassemia and anemia.

Interferons are currently used for the treatment of many viral diseases such as hepatitis B, hepatitis C, hepatitis D, condyloma acuminata, lepromatous leprosy, chronic leukaemia and AIDS. AI are also effective in reducing malignant tumors and treating Kaposi's sarcoma, melanoma, and renal cell carcinoma. Moreover, AI are applicable in the prevention and treatment of diseases in cattle and other livestock. For example, AI enhance the activity of vaccines used in prophylaxis and treatment of foot and mouth disease and porcine reproductive and respiratory syndrome.

AI have been produced from human cell lines incubated in tissue culture media or leukocytes derived from donors. However, these methods are time consuming, labor intensive, expensive, and not amenable to large scale manufacturing. Furthermore, there is the risk of septicaemia caused by infectious agents from the cell lines.

With the development of recombinant DNA technology, we can now introduce AI genes into microorganisms that enable production of large amounts of interferons. However, these methods also present certain advantages and difficulties, mainly in the steps of expression and large-scale protein production.

IL-29 is a member of the helical cytokine family and is a type III interferon. It is also known as interferon lambda 1 (IFNλ1) and is highly similar in amino acid sequence to IL-28, the other type III interferon. IL-28 and IL-29 (IFNλ1) were recently described as members of a new cytokine family that shares with type I interferon (IFN), the same Jak/Stat signaling pathway driving expression of a common set of genes. Accordingly, they have been named IFNλ. IFNsλ exhibit several common features with type I IFNs: antiviral activity, antiproliferative activity and in vivo antitumor activity. Importantly, however, IFNsλ bind to a distinct membrane receptor, composed of IFNLR1 and IL10R2.

The major disadvantage with the therapeutic use of most biologicals is that they are administered parenterally, e.g. intravenously (i.v.), subcutaneously (s.c.), intramuscularly (i.m.) etc. This means that delivery to the patient is associated with pain and discomfort. Furthermore, because of their usually very short half-lives, biologicals require frequent administration to the patient in order to maintain therapeutic blood serum or plasma levels of the drug. Injections that cannot be self-administered require frequent trips to the clinic and trained medical personnel, making such therapy inconvenient and expensive. Interferon alpha-2a (Roferon, Roche) and interferon alpha-2b (Intron A, Schering A G), the two recombinant forms of human interferon alpha used in the treatment of chronic hepatitis B and C, have a serum half-life of less than 12 h (McHutchison, et al., Engl. J. Med. 1998, 339, 1485-1492; Glue, et al., Clin. Pharmacol. Ther. 2000, 68, 556-567) and therefore require administration 3 times a week. Repeated injections with interferon beta-1b (Betaseron) are also required to treat the patients of multiple sclerosis (MS).

One very successful and well accepted method of overcoming the above requirement of frequent high dose injections to maintain threshold levels of the drug in the body is to increase the in vivo half-life of the therapeutic protein by conjugating it with a polymer, such as polyethylene glycol (PEG or Peg). PEG molecules with their long chains not only create a protective shield around the pegylated drug molecule in aqueous solution, thereby reducing the immunogenicity of protein drugs while also protecting them from the action of proteases, but they further help increase the circulation half-life of the drug by increasing its hydrodynamic volume which reduces its loss from the filtration mechanisms of the kidney glomeruli network. After their separation from the protein molecule, the PEG moieties are cleared without any structural changes and their clearance is proportional to their molecular weight.

Usually PEG moieties are attached to the protein by first activating the PEG moiety and then reacting the activated PEG agent with the side chains of an amino acid of a protein, such as the lysine residue and/or the N-terminal amino group on the protein. The most frequently used PEG is monofunctional PEG because this moiety resists cross-linking and aggregation. One such example has been disclosed by Davis et al. in U.S. Pat. No. 4,179,337.

SUMMARY OF THE INVENTION

PEG-interferon lambda 1 (PEG-IFNλ1) is a pegylated derivative of human recombinant IFNλ1 (wherein polyethylene glycol is conjugated to IFNλ1, also referred to as the "conjugate") that is useful in the treatment of chronic hepatitis C in adult patients. PEG-IFNλ1 bypasses the action of extracellular enzymes and resists filtration in the kidney after injection into the patient's body; therefore its half-life in circulation is extended. That is, the conjugate has significantly improved stability, better solubility, and enhanced circulating half-life and plasma residence times when compared to the corresponding non-PEG-conjugated IFNλ1.

Interferon lambda 1 (IFN λ1, Zcyto21 or IL-28A) is known in the art, for example, from U.S. Pat. Nos. 7,038,032, 6,927,040, 7,135,170, 7,157,559 and 7,351,689; and PCT publication Nos. WO 05/097165, WO 07/012,033, WO 07/013,944 and WO 07/041,713; all of which are herein incorporated by reference in their entirety.

In one embodiment, the present application discloses novel PEG-IFNλ1 conjugates. In one aspect, conjugates of the present application have a linear PEG chain structure. As compared to unmodified IFNλ1 (that is, the IFNλ1 that is not conjugated with PEG or mPEG), these conjugates have increased circulating half-life and persistence in plasma. Water soluble PEGs include polyethylene glycol (PEG), monomethoxy-PEG (mPEG), mono-$C_{1-10}$ alkoxy-PEG and mono-$C_{1-3}$ alkoxy-PEG. These PEGs that may be employed may have a molecular weigth of about 600 to 60,000 and include those, for example with about 10 kDa, 20 kDa, 30 kDa, 40 kDa, 50 kDa and 60 kDa. In one aspect, the PEG employed in the present conjugates are mPEG with a molecular weight of 40 kDa.

In one embodiment, there is provided a physiologically active PEG-IFNλ1 conjugate comprising the formula I:

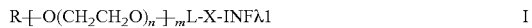

R⁅O(CH₂CH₂O)ₙ⁆ₘL-X-INFλ1    I wherein: R is H or $C_{1-3}$ alkyl; m is 1, 2, 3 or 4; n is a positive integer selected in the range from 400 to 550; L is a $C_{1-10}$ alkyl or heteroalkyl linker; X is —O—, —NH— or —S—; and IFNλ1 is interferon lambda 1; or a pharmaceutically acceptable salt thereof. In one aspect, interferon lambda 1 is a human recombinant interferon. In another aspect, the IFNλ1 may be a natural or recombinant protein. In another aspect, the IFNλ1 is a human protein derived from a source such as tissues, protein synthesis, or cell culture using natural cells or recombinant cells. In a still another aspect, IFNλ1 is a human recombinant protein. In another aspect, the conjugate interferon lambda 1 of the formula I is the SEQ ID 2. In one embodiment, the PEG chain is coupled to the IFNλ1 via an amide bond on a primary amino group of, for example, lysine, or the N-terminal of IFNλ1.

Heteroalkyl is defined as a $C_{1-10}$ alkyl wherein at least one of the carbon of the $C_{1-10}$ alkyl is replaced by an —O—, —C('O)—, —NH— or combinations thereof. Such combinations include, for example, —OC(=O)—, —C(=O)O—, —NHC(=O)—, —C(=O)NH— and the like. In one aspect, n is about 500 to 550. In another aspect, n is about 420, 520 or 455. In another aspect, the molecular weight of the Peg group is about 35 kDa to 45 kDa, or about 40 kDa. In another aspect of the above, m is 1 or 2. A $C_{1-10}$ alkyl or heteroalkyl may be a linear or a branched alkyl or heteroalkyl group. In one aspect, the $C_{1-10}$ alkyl group is a —C(O)— group. In one embodiment, m is 1 and L-X— is selected from the group consisting of the formulae:

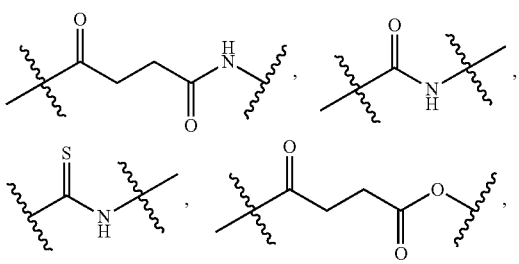

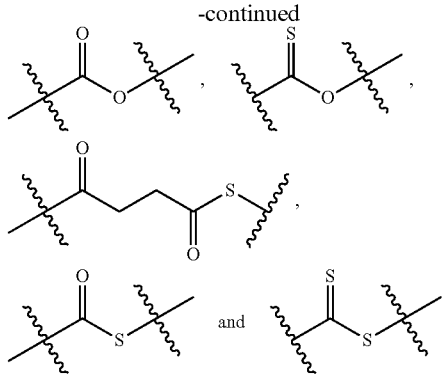

In one aspect of the above conjugate, m is 2 and L-X— is of the formula:

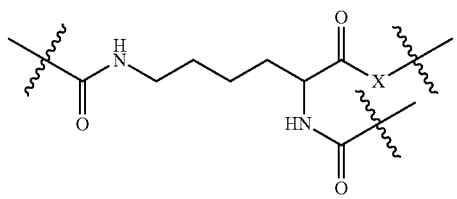

In another aspect of the above conjugate, the two PEG groups, PEG, alkyl-PEG or m-PEGs, are attached to the two formamide groups (i.e. —C(O)NH—) of the above formula. In another aspect, X is —NH— or —O— and m is 2. In another aspect, the linker is attached to two PEG groups. In another aspect, X is —NH—, and the group attached to the linker is the residue of a lysine on IFNλ1. In one aspect, the —NH— group (i.e., the amino group) attached to the linker is the residue of a histidine. In another aspect, X is —O—, and the group attached to the linker may be derived from the residue of a serine on IFNλ1. In one variation of the above formula, R is —CH₃. In another aspect, the linker is attached to the residue of a lysine, a serine, a histidine or mixtures thereof on the IFNλ1. In another aspect, the linker is attached to a positional isomer of the residue of a lysine, a serine, a histidine or mixtures thereof on the IFNλ1. In another aspect of the conjugate, R is H or —CH₃, m is 1, L is —C(O)— and X is —NH—. In another aspect, n is 500 to 550.

In another aspect, the conjugate (Nanogen PEG-IFNλ1) comprises the formula II:

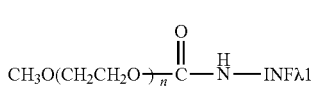

CH₃O(CH₂CH₂O⁆ₙ—C(=O)—NH—INFλ1    II wherein INFλ1 is interferon lambda 1; and n is 500 to 550. In one aspect, n is a number of units of ethylene glycol in the PEG structure and it is a positive integer selected from any numbers such that the molecular weight of PEG moiety is about 40 kDa, and INFλ1 is interferon lambda 1. In another embodiment of the above, the conjugate has a blood serum half-life and persistence time that are prolonged or extended when compared to IFNλ1. In another aspect of the conjugate, the PEG is attached to a methionine at the N-terminal of the IFNλ1. In yet another aspect, the conjugate is effective in the treatment of hepatitis B and hepatitis C.

In another embodiment, there is provided a process for the preparation of a human recombinant conjugate as disclosed above, the process comprises the step of covalently binding (α-methoxy-ω-(4-nitrophenoxy carbonyl))polyoxyethylene (PEG-pNC) 40 kDa with IFNλ1 through a conjugation reaction as follows:

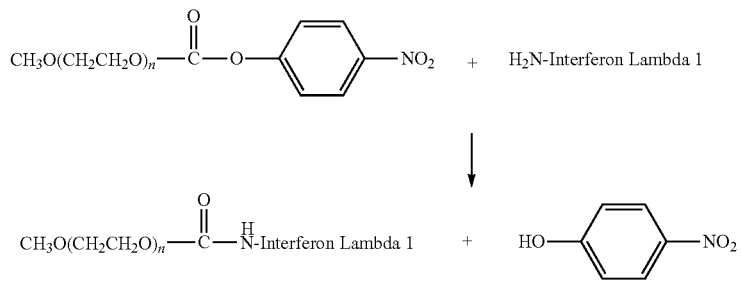

wherein, n is a positive integer selected such that the molecular weight of PEG moiety is about 40 kDa; and isolating the conjugate. In one aspect, n is from about 500 to 550.

In another embodiment, there is provided a pharmaceutical composition containing a conjugate as disclosed above and pharmaceutically acceptable carriers and excipients. Conventional pharmaceutical formulations can be also prepared using the compositions comprising the conjugate of the present application. The formulations may comprise a therapeutically effective amount of the composition comprising the conjugate together with pharmaceutically acceptable carriers as known in the art. For example, adjuvants, diluents, preservatives and/or solubilizers, if needed, may be used. Pharmaceutical compositions comprising the conjugate may include diluents of various buffers (e.g., Tris-HCl, acetate, phosphate) having a range of pH and ionic strength, carriers (e.g., human serum albumin), solubilizers (e.g., polyoxyethylene sorbitan or TWEEN®, polysorbate), and preservatives (e.g., thimerosol, benzyl alcohol), as disclosed, for example, in U.S. Pat. No. 4,496,537. In one aspect, the pharmaceutical composition is formulated as a sterile lyophilized powder for injection. In another aspect, the composition comprises a combination of pharmaceutically acceptable vehicles, including saline, buffered saline and 5% dextrose in water. In another aspect, the pharmaceutical composition is formulated as a solution for injection in vials or pre-filled syringes. In one aspect of the above, the pharmaceutical composition is used in the treatment of hepatitis B and hepatitis C. Pharmaceutical formulations and methods for preparing such formulations are well known in the art and are disclosed, for example, in *Remington, The Science and Practice of Pharmacy*, Gennaro, ed., Mack Publishing Co., Easton, Pa. 19$^{th}$ ed. 1995.

In another embodiment, there is provided a process for preparing a Peg-IFNλ1 conjugate comprising the formula I:

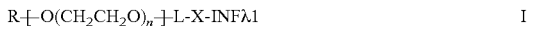    I wherein: R is H or $C_{1-3}$ alkyl; m is 1, 2, 3 or 4; n is a positive integer selected in the range from 400 to 550; L is a $C_{1-10}$ alkyl or heteroalkyl linker; X is —O—, —NH— or —S—; and IFNλ1 is interferon lambda 1; or a pharmaceutically acceptable salt thereof; the process comprising: contacting the IFNλ1 with a pre-activated Peg under conditions that are sufficient to facilitate covalent conjugation with an amino acid residue of the IFNλ1. In one embodiment, there is provided a PEG-IFNλ1 conjugate prepared by the process as described herein. In one aspect, there is disclosed a method of preparing the above conjugate comprising contacting the IFNλ1 with a sufficient amount of an activated PEG or mPEG under conditions that are sufficient to facilitate covalent attachment of the PEG or mPEG on the IFNλ1. In another aspect, the activated mPEG is mPEG-pNC. In another aspect, the attachment of the activated mPEG is on a methionine at the N-terminal of the IFNλ1. In another aspect, the mPEG has a molecular weight of about 40 kDa. In another aspect, the activated oxycarbonyl agent is a mono- or di-activated agent.

In another embodiment, there is provided a method for inhibiting the proliferation of a cancer cell in a patient comprising contacting the cancer cell with the conjugate described above, wherein the conjugate has a blood serum half-life and persistence time that are prolonged or extended when compared to IFNλ1. In one aspect, the conjugate of the present application has a blood serum half-life that is extended by more than twice, three times, five times, eight times or more than 10 times the serum half life of the corresponding unconjugated IFNλ1.

In another embodiment, there is provided a method for treating a proliferative disorder in a mammal comprising administering to the mammal a therapeutically effective amount of the above conjugate. In one embodiment, the conjugate may be used for treating interferon-susceptible conditions or conditions which would respond positively or favorably to interferon based therapy. In one aspect, the treatment using the conjugate results in substantially reduced or elimination of side effects when compared to conventional treatment with interferons.

In one aspect, exemplary conditions which can be treated with the conjugates of the present application include, but are not limited to, cell proliferation disorders, in particular cancer (e.g., hairy cell leukemia, Kaposi's sarcoma, chronic myelogenous leukemia, multiple myeloma, basal cell carcinoma and malignant melanoma, ovarian cancer and cutaneous T cell lymphoma), and viral infections. In another aspect, the conjugates may be used to treat conditions which would benefit from inhibiting the replication of interferon-sensitive viruses. Viral infections which may be treated with the conjugate of the present application include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6)), papilloma, poxvirus, picomavirus, adenovirus, rhinovirus, human T lymphotropic virus-type 1 and 2 (HTLV-1/-2), human rotavirus, rabies, retroviruses including human immunodeficiency virus (HIV), encephalitis and respiratory viral infections.

In another embodiment, there is provided a method of treating a patient infected or at risk of infection with a viral infection, comprising administering to a patient in need thereof, a therapeutically effective amount of a conjugate of the formula I:

    I wherein: R is H or $C_{1-3}$ alkyl; m is 1, 2, 3 or 4; n is a positive integer selected in the range from 500 to 550; L is a $C_{1-10}$ alkyl or heteroalkyl linker; X is —O—, —NH— or —S—; and IFNλ1 is interferon lambda 1; or a pharmaceutically acceptable salt thereof; or a pharmaceutical formulation comprising the conjugate of the formula I. In one aspect, the conjugate interferon lambda 1 of the formula I is the SEQ ID 2. In one aspect, the mammal is a human. In another aspect of the method, the viral infection is caused by a hepatitis C virus, or the viral infection results in advance liver cirrhosis. In a particular aspect, the patient is an HCV resistant or refractory patient. In another aspect of the above method, the PEG-IFNλ1 is administered in a dose of about 0.5 μg/kg to 10.0 μg/kg weekly. In one aspect of the method, the PEG-IFNλ1 is administered in a dose of about 2.5 μg/kg weekly. In another aspect, the PEG-IFNλ1 is administered for about 8 weeks to about 52 weeks. In another aspect, the PEG-IFNλ1 is administered for about 12 weeks, about 16 weeks, about 20 weeks or about 24 weeks. In another aspect, the PEG-IFNλ1 is administered until the patient is determined to be free of HCV RNA in blood serum. In another aspect, the administration of the conjugate provides significant improvement over the standard PEG-INF-α therapy because the method does not result in the significant reductions in neutrophil counts, platelet counts or hemoglobin levels. In yet another aspect of the above method, the method further comprises the administration of a nucleoside analogue selected from ribavirin and viramidine. In another aspect of the method, the ribavirin is administered orally in a dose of 5 mg/kg to 25 mg/kg daily; or 15 mg/kg to 25 mg/kg daily. In one aspect, the ribavirin is administered in a dose of about 10 mg/kg to 30 mg/kg once or twice daily, or about 15 mg/kg daily once or twice daily. In one aspect of the above, the conjugate is administered parenterally.

In one embodiment, HBV may be treated using a dose of about 200 μg of the PEG-IFNλ1 conjugate per week, combined with tenofovir (tenofovir disoproxil fumarate) at about 300 mg per day. Under this treatment, it is determined that most patients are clear of HBV after about four injections over about 30 days. Under these conditions, the HBV is found to be suppressed, and the HBsAg (virus surface antigen) is released, which triggers the immune system to make the antibody against this antigen, resulting in the optimal endpoint in the particular treatment. The treatment may be continued as disclosed herein, for about 12 weeks to 24 weeks, depending on the patient's initial viral load.

DEFINITIONS

"Alkyl" means a straight or branched, saturated or unsaturated, aliphatic radical having a chain of carbon atoms, optionally substituted with oxygen (e.g., a $C_1$ alkyl may be —C(O)—), nitrogen atoms (e.g., a $C_1$ alkyl may be —C(NH)—) or sulfur atoms (e.g., a $C_2$ alkyl may be —$CH_2C$(S)—). A $C_x$ alkyl and $C_{X-Y}$ alkyl, such as a $C_{1-10}$ alkyl or a $C_{1-6}$ alkyl, are typically used where X and Y indicate the number of carbon atoms in the chain. For example, $C_{1-6}$ alkyl includes alkyls having between 1 and 6 carbons (e.g., methyl, ethyl, propyl, isopropyl, butyl, isobutyl, vinyl, isopropenyl, 1-butenyl, ethynyl, 1-propynyl and the like).

A "heteroalkyl" or "heteroalkylene" is an alkyl that may have an oxygen, nitrogen or sulfur between the carbon atoms. Examples of such heteroalkyl groups include —C(O)NH—, —OC(O)—, —$CH_2CH_2C$(O—NH—, —$CH_2$—O—$CH_2$—$CH_2$—, —$CH_2$—NH—$CH_2$—$CH_2$—, —$CH_2$—S—$CH_2$—$CH_2$— and —$CH_2O$—$CH_2$—$CH_3$ and the like.

The term "PEG" as in "PEG-IFNλ1" means polyethylene glycol as used in the art, and generally includes both alkyl-PEG such as mPEG (methoxy-polyethylene glycol) and PEG, unless specified otherwise.

A "therapeutically effective amount" is an amount of the PEG-IFNλ1 conjugate that is sufficient to produce a clinically significant change in the treated condition, such as a clinically significant change in the viral load or immune function, a significant reduction in morbidity or a significantly increased histological score, or combinations thereof.

As used herein, "treatment" or "treating" refers to a therapeutic treatment and prophylactic or preventive measures. Patients who are in need of treatment include patients already infected with hepatitis C virus as well as those in which the hepatitis C disease is to be prevented.

In one aspect of the above method, the conjugate is administered by injection or infusion. In another aspect, the conjugate is administered intravenously, intramuscularly, subcutaneously, intradermally or intraperitoneally. In another aspect, the conjugate is administered to the patient in a dose amount selected from less than 0.5 μg/kg, 0.5 to 1.0 μg/kg, 1.0 to 1.5 μg/kg, 1.5 to 2.0 μg/kg, 2.0 to 2.5 μg/kg, 2.5 to 3.0 μg/kg, 3.0 to 3.5 μg/kg, 3.5 to 4.0 μg/kg, 4.0 to 4.5 μg/kg, 4.5 to 5.0 μg/kg, 5.0 to 5.5 μg/kg, 5.5 to 6.0 μg/kg, 6.0 to 6.5 μg/kg, 6.5 to 7.0 μg/kg, 7.0 to 7.5 μg/kg, 7.5 to 8.0 μg/kg, 8.0 to 8.5 μg/kg, 8.5 to 9.0 μg/kg, 9.0 to 9.5 μg/kg, 9.5 to 10.0 μg/kg, or greater than 10.0 μg/kg. In another aspect, the conjugate is administered in a fixed dose of about 60-80 μg, 80-100 μg, 100-120 μg, 120-140 μg, 140-160 μg, 160-180 μg, 180-200 μg, 200-220 μg, 220-240 μg, 240-260 μg, 260-280 μg, or about 280-300 μg. In one embodiment, the conjugate is administered subcutaneously at 200 μg for 12 consecutive weeks.

In another embodiment, there is provided a pharmaceutical composition containing the above conjugate and pharmaceutically acceptable carriers and excipients. In another aspect, the pharmaceutical composition is used in treatment of hepatitis B and hepatitis C. In another embodiment, there is provided a process for the preparation of a pharmaceutical composition containing the above conjugate comprising mixing the conjugate with pharmaceutically acceptable carriers and excipients.

The conjugates of the application have similar effects or activities as those of IFNλ1. For example, the conjugates may be used as anti-proliferative agents, antiviral agents, or anti-tumor agents. Specifically, the conjugates of the present application are effective in treatment of hepatitis B and hepatitis C, and they have a longer persistence time in blood than IFNλ1. In one embodiment, pharmaceutical compositions containing the conjugates of the present application are prepared as sterile lyophilized powders for injection, or as solutions for injection in vials or pre-filled syringes. These pharmaceutical compositions may be formulated by mixing the conjugates with relevant pharmaceutically acceptable carriers and excipients.

In another embodiment, the present application provides processes for the preparation of human recombinant PEG-IFNλ1 conjugates. First, human recombinant IFNλ1 is produced by recombinant DNA technology in *E. coli*, then reacted with a pegylating agent (such as α-methoxy-ω-(4-nitrophenoxy carbonyl))polyoxyethylene (PEG-pNC) to produce the PEG-IFNλ1. In one aspect, the PEG-IFNλ1 is a linear chain PEG 40 kDa that is conjugated to IFNλ1. This product bypasses the action of extracellular enzymes and kidney filtration when injected into the patient's body, therefore its blood serum half-life is extended.

The pegylation reaction between (α-methoxy-ω-(4-nitrophenoxy carbonyl))polyoxyethylene (PEG-pNC) 40 kDa and IFNλ1 to form the conjugate, is shown below. In one aspect, the —NH$_2$ group is a methionine residue at the N-terminal on a site of the interferon lambda 1 molecule. In another aspect, the —NH$_2$ group is the amine of a lysine residue on a site of the interferon lambda 1 molecule.

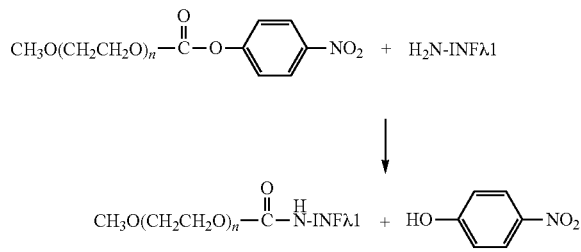

In one embodiment, the conjugates of the present application may be prepared by covalently binding Interferon lambda 1 with pre-activated PEG. In one embodiment, PEG may be activated by substituting the PEG hydroxyl group with a linking group to form the coupling agent, or an activated PEG agent that is (α-methoxy-ω-(4-nitrophenoxy carbonyl))polyoxyethylene (PEG-pNC). In one embodiment, the PEG-IFNλ1 conjugates may be prepared by the preparation of IFNλ1 and the pegylation of the IFNλ1. Also disclosed are processes for purifying and assaying the conjugated products.

BRIEF DESCRIPTION OF THE DRAWINGS

FIG. 1 exemplifies a nucleic acid sequence (SEQ ID 1) used to produce human recombinant IFNλ1 after the sequence was synthesized and introduced into the expression vector pNanogen 1-IL29.

FIG. 2 is a representative amino acid sequence (SEQ ID 2) of human recombinant IFNλ1 produced by Nanogen Pharmaceutical Biotechnology Co., Ltd.

DETAILED DESCRIPTION OF THE INVENTION

In one embodiment, the present application discloses processes for preparing a recombinant bacterial strain containing the gene encoding IFNλ1, large scale or industrial manufacture of IFNλ1, pegylation reaction of IFNλ1, purification of the produced the PEG-IFNλ1, and assays of PEG-IFNλ1.

In one embodiment, the present application discloses an artificial synthesis of the gene encoding IFNλ1 based on the published sequence available from the National Center for Biotechnology Information (the encoding gene was modified to conform to the industrial production process on E. coli), creating of the gene transfer vectors, introducing these vectors into the bacteria, and selecting the bacterial strain that best produced IFNλ1.

In one embodiment, the industrial manufacturing process for IFNλ1 includes the steps of: fermenting the initial material, collecting the solution of crude proteins and purifying the IFNλ1 protein. In a representative process, the fermentation process may be carried out in a 10 liter fermenting tank containing a nutrient medium and production of IFNλ1 was induced by lactose. The biomass obtained was separated and purified. IFNλ1 was collected and refined through a number of steps including: refolding the protein, separating the protein, for example by ion exchange chromatography (cation 1 and cation 2), and refining the protein on a gel.

In one embodiment, the pegylation process comprises a reaction between the linear chain (α-methoxy-ω-(4-nitrophenoxy carbonyl))polyoxyethylene (PEG-pNC- with a molecular weight of 40 kDa) and IFNλ1. The resulting conjugate product may be purified by chromatography, such as using an HPLC system, and tested for quality and purity.

The present application will be more fully appreciated by reference to the following examples, which are to be considered merely illustrative and not limiting to the scope of the invention as claimed.

EXAMPLES

Example 1

Process for Preparing E. coli Strain Containing the Gene Encoding Human Recombinant Interferon Lambda 1 (IFNλ1)

The gene encoding IFNλ1 was artificially synthesized based on the protein sequence data available from NCBI or other databases. The novel method provided herein reduces the time required to isolate the gene but still provides a result as accurate as the conventional method. The nucleic acid sequence used to produce IFNλ1 in Nanogen Pharmaceutical Biotechnology Co., Ltd. is shown in FIG. 1 and the amino acid sequence of this protein is shown in FIG. 2.

Figure 3:
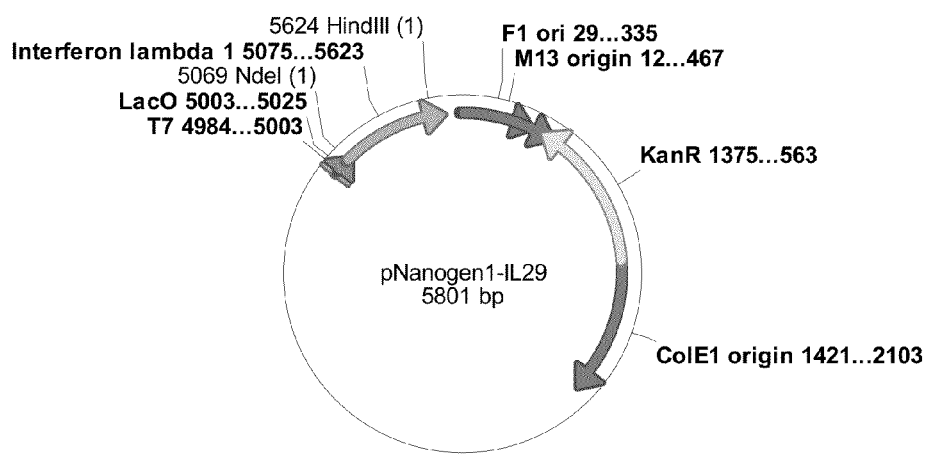
FIG. 3 exemplifies a plasmid pNanogen 1-IL29 containing the gene encoding human IFNλ1 (interleukin-29).
Figure 4:
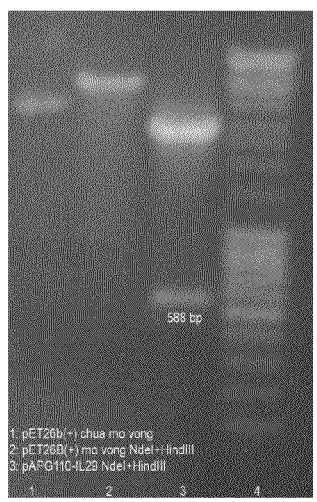
FIG. 4 depicts a result of analyzing plasmid pNanogen 1-IL29.

The expression vector pNanogen-IL29 (comprising the T7 transcription promoter region, the IFNλ1 transgene, the T7 reverse priming site, the T7 transcription terminator, the f1 origin, the kanamycin resistance gene, and the pUC origin of replication) was specifically designed to enable high expression of the protein and facilitate fermentation for industrial production of a large quantity of IFNλ1. FIGS. 3, 4 show the process for creation of vector pNanogen 1-IL29.

Figure 5:
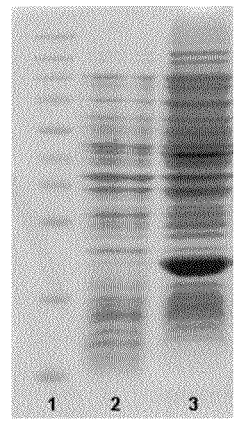
FIG. 5 exemplifies a result of an electrophoresis process for examining the ability of E. coli containing pNanogen 1-IL29 used to produce IFNλ1.
Figure 6:
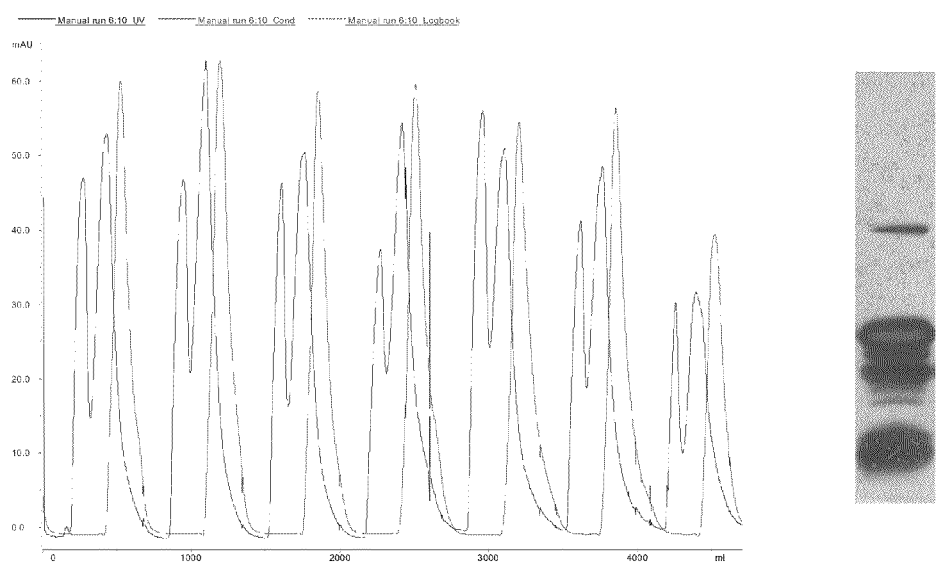
FIG. 6 is a representative spectrum of the salt phase and SDS-PAGE electrophoresis after refolding protein. The spectrum of FIGS. 6, 7, 8 and 9 are all coomassi blue stained.
Figure 7:
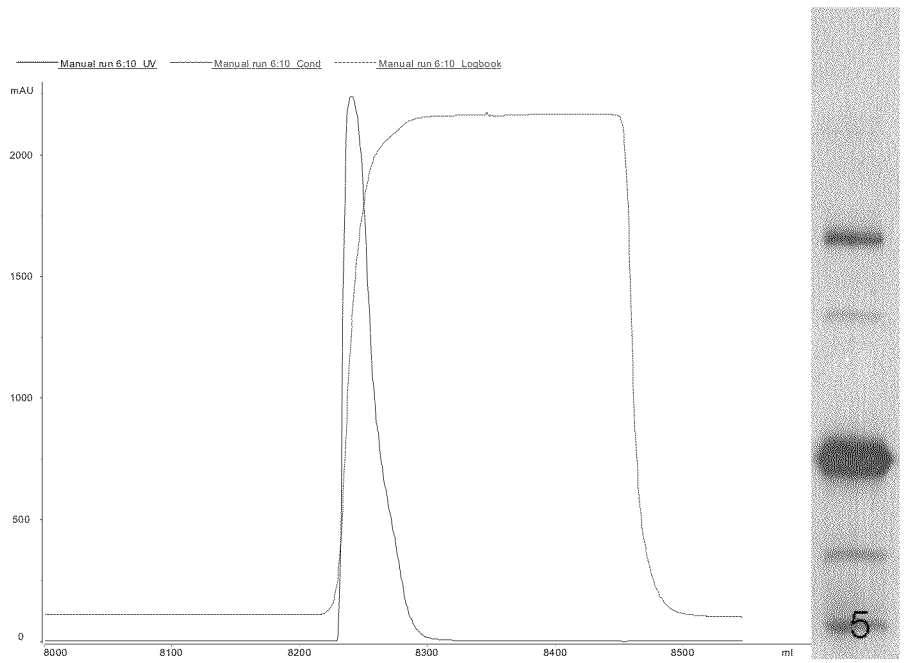
FIG. 7 exemplifies a spectrum and SDS-PAGE electrophoresis after cation 1 phase.
Figure 8:
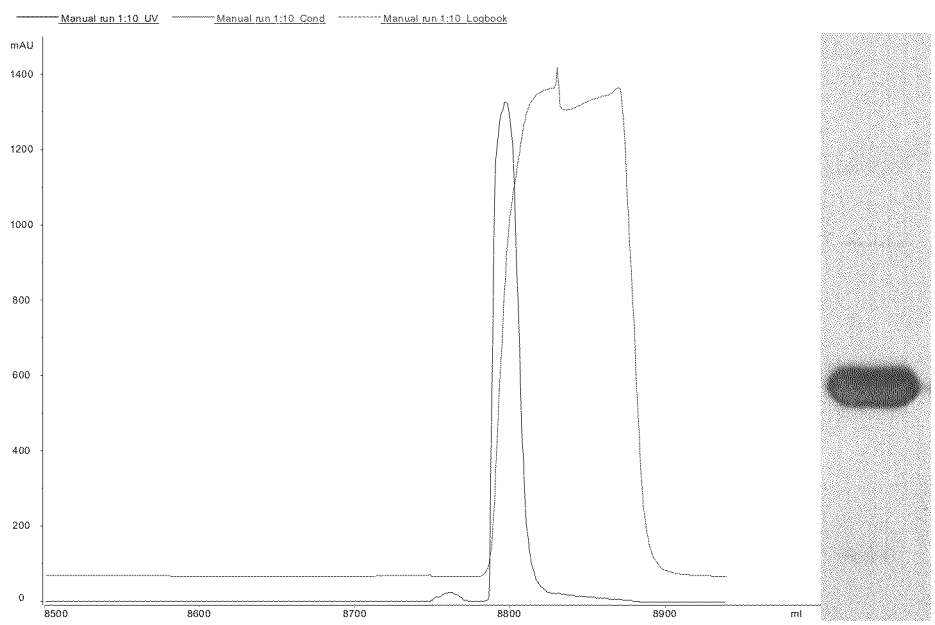
FIG. 8 exemplifies a spectrum and SDS-PAGE electrophoresis after cation 2 phase.
Figure 9:
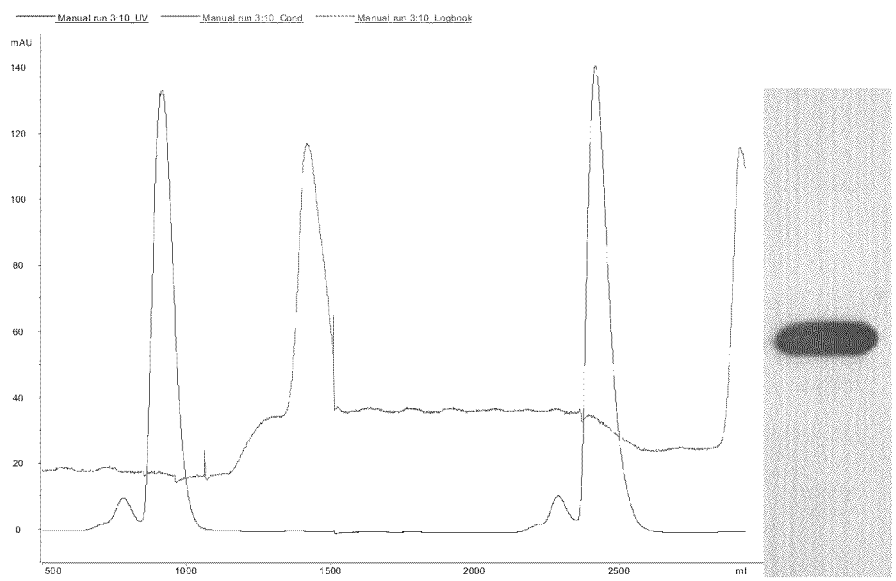
FIG. 9 exemplifies a spectrum and SDS-PAGE electrophoresis after a gel filtration phase.

Vector pNanogen 1-IL29 was then transferred into an E. coli strain suitable for expression of promoter T7. This strain has a genotype F$^-$ ompT hsdS$_B$ (rR$^-$mB$^-$)gal dcm (DE3). The strain containing the IFNλ1 gene is termed E. Coli-pNanogen1-IL29. It has the ability to produce higher than 100 mg of IFNλ1 per liter by fermentation (see FIG. 5) and was introduced into the original strain bank.

Example 2

Process for Fermentation of *E. coli* to Produce Human Recombinant IFNλ1

The fermentation process was carried out in a 140 liter fermentation tank with nutrient medium at a temperature of 37±0.5° C., air pressure 0.5 m³/h, pH 7.0±0.2, stirring rate of 300 rpm and the pH was maintained at between 6.8-7.2 by adding $H_3PO_4$ or $NH_4OH$. After 8 hours (when *E. coli* grew in log phase is the time that cells develop most efficiently), the temperature was cooled to 30±0.5° C. and the stirring rate was reduced to 200 rpm to start the process for the generation of IFNλ1. The fermentation process was stopped after 4 hours and the cold product was centrifuged at 6000 rpm to obtain biomass.

The biomass was disrupted in a cell lysis solution (12 ml solution per 1 g wet biomass) by homogenizing in a homogenizing device. The temperature was maintained at 4° C. for 1 hour, then the cells were disrupted 2 times by an ultrasonic device. The resulting suspension was centrifuged at 6000 rpm for 30 minutes to give a pellet. The pellet was then washed with an inclusion body wash buffer (12 ml buffer per 1 g wet biomass), the resulting suspension was kept at 4° C. for 1 hour, then centrifuged twice at 13,000 rpm for 30 minutes to obtain a pellet. The pellet was dissolved in 2M urea solution and incubated ice-cold for 1 hour, the suspension was then centrifuged at 13,000 rpm for 30 minutes to give the pellet. The pellet was dissolved in a wash solution and centrifuged at 13,000 rpm for 30 minutes to give a resulting pellet. The pellet was then dissolved in 6M guanidine solution, the suspension was kept ice-cold for 12-16 hours, and centrifuged at 13,000 rpm for 30 minutes. The solution containing protein was recovered and purified in next step.

The components of culture medium and solutions used to separate IFNλ1 are shown in Table 1.

TABLE 1

| | |
|---|---|
| Culture medium of *E. coli*-pNanogen1 - IL29 bacteria | 70 µg/ml Kanamycin |
| | 2 mM MgSO4 |
| | 0.1% aspartate |
| | 25 mM Na₂HPO₄ |
| | 25 mM KH₂PO₄ |
| | 50 mM NH₄Cl |
| | 5 mM Na₂SO₄ |
| | 0.5% Glycerol |
| | 0.05% Glucose |
| | 0.2% α-lactose |
| | 200 µg/ml each amino acid (18) |
| Cell lysis solution | NaCl 50 mM |
| | EDTA 1 mM |
| | Tris base 20 mM |
| Inclusion body wash solution | EDTA 1 mM |
| | Tris base, pH 8, 20 mM |
| | Triton X100 1% |
| Wash solution | EDTA 1 mM |
| | Tris base 20 mM |
| 6M guanidine solution | EDTA 2 mM |
| | Tris base 50 mM |
| | Guanidine 6M |
| | Cysteine HCl 75 mM |

Example 3

Process for Purification of Human Recombinant IFNλ1

IFNλ1 was refolded by dissolving the inclusion bodies in refolding solution (25 mM Tris buffer, 1 mM EDTA, 1.2M guanidine, pH 8.2) such that the final concentration of the inclusion bodies were 500 µg/ml. The mixture was then kept at 2-8° C. for 16-24 hours. The resulting mixture was desalted before being subjected to a purification step on a Sephadex G25 column. The salt exchange buffer was a phosphate buffer (10 mM, pH 8.0). In the step "cation 1", the desalted mixture was loaded onto a Sephadex G25 column (this column was prefilled with CM-Sepharose FF gel and equilibrated in 10 mM phosphate buffer pH 8.0), the product was eluted using 10 mM sodium phosphate+0.5M NaCl pH 8.0. The resulting protein solution was desalted and chromatographed as above (step "cation 2"). The protein solution was then filtered through a gel column to give the product human recombinant IFNλ1 with purity greater than 95% (see the spectrum and electrophoresis results in FIGS. 5, 6, 7, 8 and 9).

Example 4

Pegylation Process for Preparing the Conjugate

The solution of 5 mg/ml human recombinant IFNλ1 (MW~20.1 kDa) in 50 mM sodium borate-phosphate pH 8.0 was added (α-methoxy-ω-(4-nitrophenoxy carbonyl))poly-oxyethylene (PEG-pNC) (MW~40 kDa) at a molar ratio of PEG-pNC:IFNλ1 about 3:1. The reaction mixture was kept at 2-4° C. for 20 hours. The reaction was stopped by adjusting the pH to 4.0 using 30% w/w acetic acid solution. The resulting mixture was then diluted 5-fold with water.

In a general exemplary process, the reaction conditions for the conjugation reaction of the activated PEG or m-PEG reagent to the IFNλ1 further include conducting the reaction using about equi-molar to a relatively small molar excess of the activated PEG or m-PEG with respect to IFNλ1. In one variation, the conjugation may be carried out with about 1-10 fold molar excess; or about 1.5 to 7 fold molar excess; or about 1.75 to 5 fold molar excesses. In one variation, the conjugation reaction can be carried out at about room temperature, or about 20-25° C. The conjugation reaction may be allowed to proceed for about 1 to 10 hrs, 1 to 5 hrs, 1 to 3 hrs or about 1 to 2 hrs, before the reaction is terminated by quenching. In some cases, the reaction conditions provide a mixture of the PEG-IFNλ1 positional isomers. In one aspect, each isomer contains a single PEG-linker unit attached to the IFNλ1 via an amino acid residue as disclosed herein. In certain cases where more than one PEG-linker unit is attached to an IFNλ1, if desired, the resulting composition containing these conjugates may be used or may be separated by chromatography using standard purification methods, including ultrafiltration, ion exchange chromatography, affinity chromatography and size exclusion chromatography. In one aspect, the purification method used for the separation and purification of the conjugates is cation exchange chromatography as described herein.

In certain conditions, the site of conjugation on the IFNλ1 may be influenced by the pH of the reaction medium. Modification of the particular pH of the conjugation process will result in certain preferred sites of conjugation. For example, under certain conditions, the conjugation at basic pH values, such as pH of 7.5 or higher, 8.0 or higher, 8.5 or higher or 9.0 or higher, favors the conjugation to a lysine group of the IFNλ1.

In the above method, the pegylation reagent, such as PEG-pNC, forms a carbamate linker between the PEG and IFNλ1. Additional pegylation reagents that may be employed in the above process include oxycarbonyl-oxy-N-dicarboximide (such as succinimidyl carbonate, succinimidyl succinate), para-nitroaryl carbonates, para-nitrophenyl carbonates, carbonyl di-imidazole, benzotriazole carbonates, pyridyl carbonates, N-succinimide, N-phthalimide, N-glutarimide, and N-tetrahydrophthalimide as disclosed in U.S. Pat. No. 5,122,614. Representative activated PEG or mPEG compounds that may be used to form the conjugate include PEG-2,4,6-trichloro-S-triazine, mPEG-2,4,6-trichloro-S-triazine, PEG-N-succinimidyl glutarate, mPEG-N-succinimidyl glutarate, PEG-N-succinimidyl succinate and mPEG-N-succinimidyl succinate.

Representative Compounds of the Examples:

The following Table provides a summary of selected compounds of the Examples as described herein:

Ia $$R-O(CH_2CH_2O)_n-L-X-INF\lambda 1$$

| Conjugates | R | n (kDa) | —L— | —X— |
|---|---|---|---|---|
| 1 | CH$_3$— | 900-945 (40) | —C(=O)— | —NH— |
| 2 | CH$_3$— | 900-945 (40) | —C(=O)— | —O— |
| 3 | CH$_3$— | 900-945 (40) | —C(=O)— | —S— |
| 4 | CH$_3$— | 790-830 (35) | —C(=O)— | —NH— |
| 5 | CH$_3$— | 790-830 (35) | —C(=O)— | —O— |
| 6 | CH$_3$— | 790-830 (35) | —C(=O)— | —S— |
| 7 | CH$_3$— | 1,010-1,060 (45) | —C(=O)— | —NH— |
| 8 | CH$_3$— | 1,010-1,060 (45) | —C(=O)— | —O— |
| 9 | CH$_3$— | 1,010-1,060 (45) | —C(=O)— | —S— |
| 10 | CH$_3$— | 900-945 (40) | 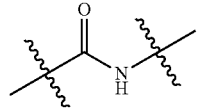 [SMILES: *NC(*)=O] | —NH— |
| 11 | CH$_3$— | 900-945 (40) | 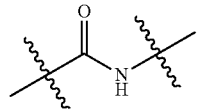 [SMILES: *NC(*)=O] | —O— |
| 12 | CH$_3$— | 900-945 (40) | 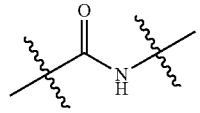 [SMILES: *NC(*)=O] | —S— |
| 13 | CH$_3$— | 900-945 (40) | 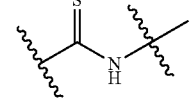 | —NH— |
| 14 | CH$_3$— | 900-945 (40) | 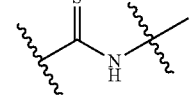 | —O— |
| 15 | CH$_3$— | 900-945 (40) | 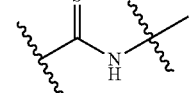 | —S— |
| 16 | CH$_3$— | 900-945 (40) | 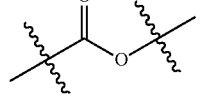 | —NH— |

-continued
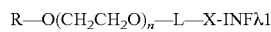
Ia
|  |  | n |  |  |
|---|---|---|---|---|
| Conjugates | R | (kDa) | —L— | —X— |
| 17 | CH₃— | 900-945 (40) | —C(=O)—O— (ester) | —O— |
| 18 | CH₃— | 900-945 (40) | —C(=O)—O— (ester) | —S— |
| 19 | CH₃— | 900-945 (40) | —C(=S)—O— | —NH— |
| 20 | CH₃— | 900-945 (40) | —C(=S)—O— | —O— |
| 21 | CH₃— | 900-945 (40) | —C(=S)—O— | —S— |
| 22 | CH₃— | 900-945 (40) | —C(=O)—S— | —NH— |
| 23 | CH₃— | 900-945 (40) | —C(=O)—S— | —O— |
| 24 | CH₃— | 900-945 (40) | —C(=O)—S— | —S— |
| 25 | CH₃— | 900-945 (40) | —C(=S)—S— | —NH— |
| 26 | CH₃— | 900-945 (40) | —C(=S)—S— | —O— |
| 27 | CH₃— | 900-945 (40) | —C(=S)—S— | —S— |

-continued
R—O(CH₂CH₂O)ₙ—L—X-INFλ1    Ia
Variables
| Conjugates | R | n (kDa) | —L— | —X— |
|---|---|---|---|---|
| 28 | CH₃— | 900-945 (40) | 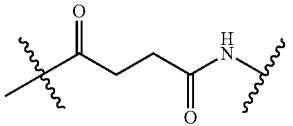 | —NH— |
| 29 | CH₃— | 900-945 (40) | 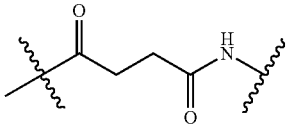 [SMILES: *NC(=O)CCC(*)=O] | —O— |
| 30 | CH₃— | 900-945 (40) | 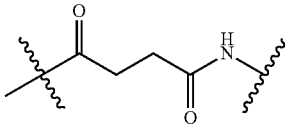 [SMILES: *NC(=O)CCC(*)=O] | —S— |
| 31 | CH₃— | 900-945 (40) | 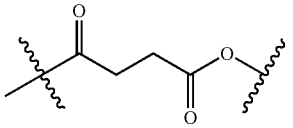 [SMILES: *OC(=O)CCC(*)=O] | —NH— |
| 32 | CH₃— | 900-945 (40) | 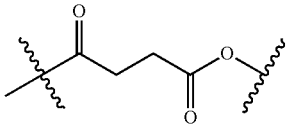 [SMILES: *OC(=O)CCC(*)=O] | —O— |
| 33 | CH₃— | 900-945 (40) | 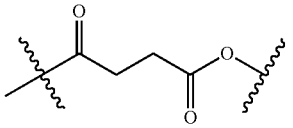 | —S— |
| 34 | CH₃— | 900-945 (40) | 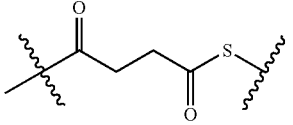 [SMILES: *SC(=O)CCC(*)=O] | —NH— |
| 35 | CH₃— | 900-945 (40) | 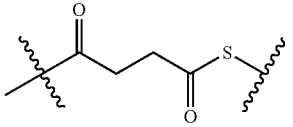 [SMILES: *SC(=O)CCC(*)=O] | —O— |
| 36 | CH₃— | 900-945 (40) | 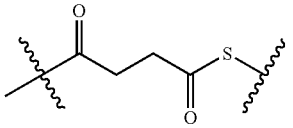 [SMILES: *SC(=O)CCC(*)=O] | —S— |
| 37 | CH₃— | 900-945 (40) | 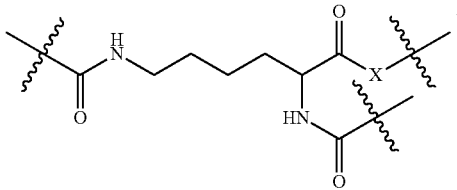 | —NH— |

-continued $$R-O(CH_2CH_2O)_n-L-X-INF\lambda1 \quad Ia$$

Variables

| Conjugates | R | n (kDa) | —L— | —X— |
|---|---|---|---|---|
| 38 | CH$_3$— | 900-945 (40) | lysine-based linker | —O— |
| 39 | CH$_3$— | 900-945 (40) | lysine-based linker | —S— |
| 40 | H— | 900-945 (40) | —C(=O)— | —NH— |
| 41 | H— | 900-945 (40) | —C(=O)— | —O— |
| 42 | H— | 900-945 (40) | —C(=O)— | —S— |
| 43 | H— | 900-945 (40) | lysine-based linker | —NH— |
| 44 | H— | 900-945 (40) | lysine-based linker | —O— |
| 45 | H— | 900-945 (40) | lysine-based linker | —S— |

Processes for the purification of the conjugates of the formula Ia in the above table are performed using the methods described herein. The resulting PEG-IFNλ1 has a purity that is higher than about 95%. A spectrum and SDS-PAGE electrophoresis of the conjugate after a gel filtration phase is exemplified in FIG. 9. A spectrum of the purification process and SDS-PAGE electrophoresis of the conjugate is exemplified in FIG. 10. The conjugates have antiviral EMC activity on Hep-2C cell with ED$_{50}$ in a range of about 10-50 ng/ml. Antiviral activities of the conjugates of the formula Ia in the above table at ED$_{50}$ (ng/ml) are about 25.00 to 28.00; with a Mean (ng/ml) of about 1.0 to about 30.0; SD of about 0.1 to about 1.0 and RSD of about 3.0 to 7.0.

The conjugates of the formula Ia in the above table are administered to patients at 200 μg (weekly subcutaneous injection)+ribavirin 15 mg/kg (daily). In the first 4 weeks, all patients are determined to be free of HCV RNA (free virus in serum). The treatment protocols are continued for 12 weeks. All patients achieve primary endpoint of total viral surpression after 12 weeks treatment and 12 weeks follow up.

Example 5

Purification of PEG-IFNλ1

The solution containing PEG-IFNλ1, quenched reagent and unmodified IFNλ1 was purified on a cation column (this column was prefilled with Sepharose CM gel and equilibrated in 10 mM sodium phosphate pH 6.0, eluted with a solution of 10 mM sodium phosphate, 0.5M NaCl pH 6.0. The eluted fractions containing protein were transferred into preservative buffer using a solution of 10 mM sodium phosphate pH 6.0. This product was then subjected to a sterile filtration process and stored at −20° C.

Figure 10:
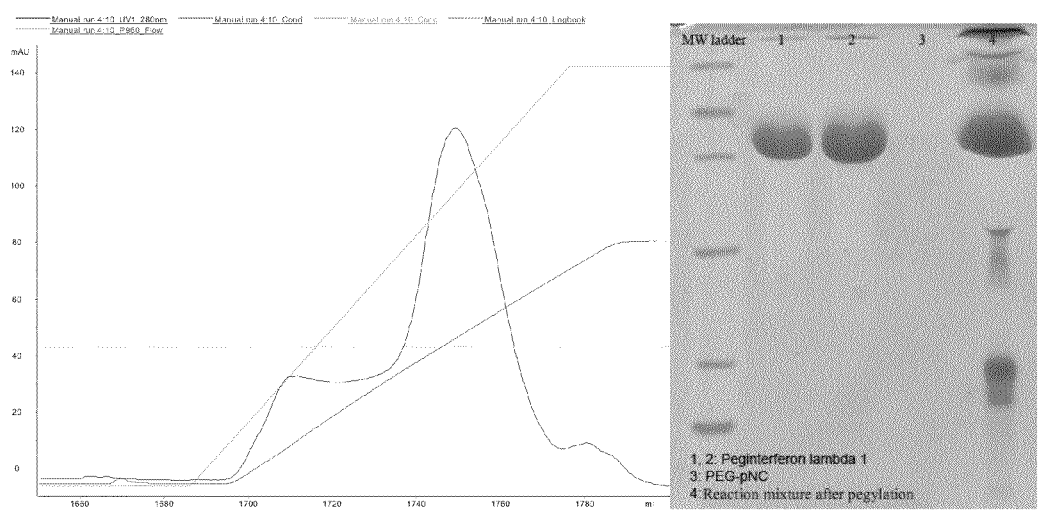
FIG. 10 exemplifies a spectrum of the purification process and SDS-PAGE electrophoresis of PEG-interferon lambda 1.

FIG. 10 shows the spectrum of the purification process and SDS-PAGE electrophoresis of IFNλ1. The resulting PEG-IFNλ1 had a purity that is higher than 95% and antiviral EMC activity on Hep-2C cell with $ED_{50}$ about 10-50 ng/ml (see example 6).

Example 6

Examination of antiviral activity of IFNλ1 and PEG-IFNλ1

The examination was based on the antiviral activity in EMC viral model and Hep-2C cell according to the study of Ank et al. (J Virol. 2006 May; 80(9):4501-9). The experiment was carried out with 3 lots (IL290010111, IL290020311 and IL290030411). The results indicated that the antiviral activity of Nanogen's interferon lambda 1 ($ED_{50}$ about 1-5 ng/ml) is equivalent to the study results of Sheppard et al. (Nat Immunol. 2003 January; 4(1):63-8.) (see Table 2).

The antiviral activity of PEG-IFNλ1 was compared to IFNλ1. The experiments were carried out with 5 lots (PIL290010111, PIL290020211, PIL290030311, PIL290040411, PIL290050511). Similar results were obtained in all lots, with an $ED_{50}$ about 10-50 ng/ml (see Table 3).

Patients' Clinical Information Prior to Treatment:

All patients in this treatment group were diagnosed with HCV chronic have been previously treated with Pegasys (PegInterferon alfa 2a) and PegIntron (PegInterfeon alfa 2b) combined with ribavirin (15 mg/kg) for over six months with no HCV RNA reduction of more than one log. HCV RNA 22 500,000 IU/ml serum; HCV Genotype 1-6; quantity 150; Age 26-78 years old; median age 52 yr; some patient with high Ferritin, low Platelet (<50,000/ml), low Hb. Most patients have high level of fibrosis on the Fibro scale of F4 due to being chronically infected with HCV, where high AST/ALT ratio over 1 indication of liver fibrosis. Some of the patients were under insulin treatment for diabetes. All patients in the treatment group that are over 50 years old have high blood pressure.

Treatment Regimen:

Peglamda (PEG-IFNλ1) 200 μg (weekly subcutaneous injection)+ribavirin 15 mg/kg (daily). First 4 weeks, all patients were determined to be free of HCV RNA (free virus in serum). The treatment was continued for 12 weeks.

Results: All patients achieved primary endpoint of total viral suppression after 12 weeks treatment and 12 weeks follow up.

TABLE 2

Antiviral activity of Nanogen's interferon lambda 1 (PEG-IFNλ1)

|  | Lot IL290010111 | Lot IL290020311 | Lot IL290030411 |
|---|---|---|---|
| $ED_{50}$ (ng/ml) | 1.23 | 2.10 | 1.99 |
| Mean (ng/ml) |  | 1.97 |  |
| SD |  | 0.13 |  |
| RSD |  | 6.78 |  |

TABLE 3

Antiviral activity of Nanogen's PEG-IFNλ1

|  | Lot PIL 290010111 | Lot PIL 290020211 | Lot PIL 290030311 | Lot PIL 290040411 | Lot PIL 290050511 |
|---|---|---|---|---|---|
| $ED_{50}$ (ng/ml) | 26.94 | 28.70 | 26.27 | 26.00 | 27.31 |
| Mean (ng/ml) |  |  | 27.04 |  |  |
| SD |  |  | 1.06 |  |  |
| RSD |  |  | 3.92 |  |  |

Therapy for HCV Resistant Patients:

More than 50 patients who have been previously treated using standard therapies, such as a combination of PEGASYS® (peginterferon alfa-2a) with ribavirin, were found to be ineffective. The non-responder patients, defined by the guidelines for HCV treatment from AASLD as patients who do not show a clearance of HCV RNA from serum from 24 weeks of therapy, and the null-responder patients, defined as those who show a failure to decrease HCV RNA at the $12^{th}$ week by >2 log, were enrolled in the treatment regiment using the PEG-IFNλ1 of the present application.

After 4-12 weeks or 4-24 weeks of treatment with PEG-IFNλ1 using the disclosed treatment protocol, substantially all patients were tested and determined to be HCV RNA negative; or all patients had a sustained virological response (SVR), defined as having no detectable virus 24 weeks after the final treatment dose.

In other studies using HCV resistant patients, the presently disclosed treatment protocol was found to be effective for greater than 80%, 85%, 90% or greater than 95% of the HCV resistant patient population. Accordingly, the treatment methods using the PEG-IFNλ1 demonstrate efficacy in HCV including cases of resistance to current standard therapy of peginterferon alfa-2a with ribavirin. No significant side effects that are typically associated with the combination therapy of PEGASYS® with ribavirin were observed.

Example 7

Identification of IFNλ1 and PEG-IFNλ1

Figure 11:
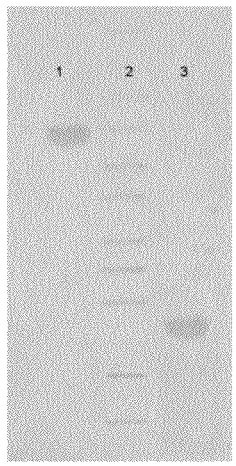
FIG. 11 exemplifies an identification results of IFNλ1 and PEG-IFNλ1.

Western blotting method was used to identify IFNλ1 and PEG-IFNλ1 using anti-IFNλ1 antibody. The protein solution after being analyzed on an SDS-PAGE gel was transferred to a nitrocellulose membrane and probed with the anti-IFNλ1 antibody. Antibody was detected with peroxidase coupled protein A and TMB substrate (see FIG. 11).

Example 8

Molecular Weight of PEG-IFNλ1

Figure 12:
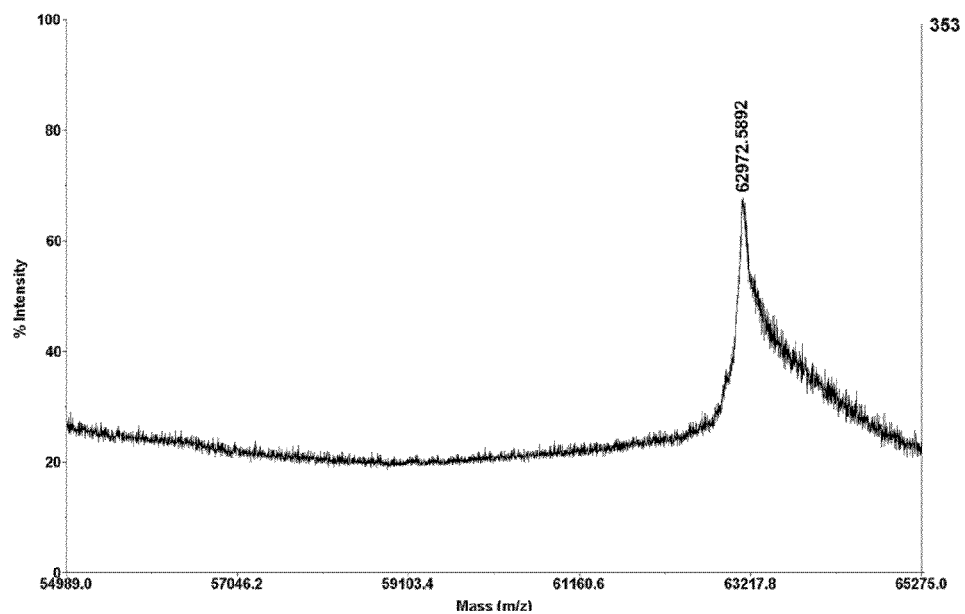
FIG. 12 exemplifies a Maldi-Tof mass-spectrum of PEG-IFNλ1 produced by Nanogen Pharmaceutical Co., Ltd.

The MALDI-TOF assay was applied to determine the molecular weight of PEG-IFNλ1. The result is provided in FIG. 12. In the present example, the Nanogen's PEG-IFNλ1 has a molecular weight of approximately 62 kDa.

Example 9

Purity of PEG-IFNλ1

Five lots (PIL290010111, PIL290020211, PIL290030311, PIL290040411, PIL290050511) were used to determine the purity of PEG-IFNλ1 by SDS-PAGE electrophoresis. The electrophoresis gel was stained with coomassie blue, destained and then analyzed using Phoretix software (TotalLab, England). All tested lots showed purity higher than 95%.

The following tests employ the PEG-IFNλ1 as prepared above:

Example 10

Toxicity of PEG-IFNλ1

Acute toxicity of PEG-IFNλ1: The acute toxicity of PEG-IFNλ1 was assessed in Swiss mice and rats. Healthy ICR mice and Sprague-Dawley rats, at 5 week old, were chosen for the study. The animals were inspected for two weeks. PEG-IFNλ1 was administered at three different dosages (high dose 3 mg/kg, medium dose 0.3 mg/kg, low dose 0.03 mg/kg and the vehicle treatment (phosphate buffer saline, pH 7.2)) by subcutaneous or intraperitoneal injection. Animals were observed for clinical signs, body weight changes, and mortality 14 days after treatment. At the end of the study, all animals were sacrificed, and their tissues and organs were examined for abnormalities. The results are summarized in table 4.

TABLE 4

| | Experiment | | | | | Results | | |
|---|---|---|---|---|---|---|---|---|
| Animal | Number of animals | Administration route | Administration period | Dose (mg/kg) | Volume (ml) | Body weight | Clinical signs | Autopsy result |
| Swiss mice | 5 males, 5 females | Intraperitoneal injection | Once a week | 3<br>0.3<br>0.03 | 0.5 | No significant difference (*) | None | No abs.[1] |
| Rats | 5 males, 5 females | Intraperitoneal injection | Once a week | 3<br>0.3<br>0.03 | 1.0 | No significant difference (*) | None | No abs.[1] |
| Swiss mice | 5 males, 5 females | Subcutaneous injection | Once a week | 3<br>0.3<br>0.03 | 0.5 | No significant difference (*) | None | No abs.[1] |
| Rats | 5 males, 5 females | Subcutaneous injection | Once a week | 3<br>0.3<br>0.03 | 1.0 | No significant difference (*) | None | No abs.[1] |

(*): ANOVA, single factor, compare to the vehicle treatment, (p > 0.05)
[1]means no abnormalities All animals survived for the test period even at the highest dosage. The body weight did not significantly change in the treated animals compared to the control. There were no clinical signs or organ abnormalities observed in either group of the tested animals.

Based on these results, the lethal dose (LD50) of Nanogen's PEG-IFNλ1 in mouse and rat was greater than 3 mg/kg. Subacute toxicity of PEG-IFNλ1: Animals (5 weeks old rats) were administered PEG-IFNλ1 at three different dosages (high dose 3 mg/kg, medium dose 0.3 mg/kg, low dose 0.03 mg/kg) by subcutaneous or intraperitoneal injection once a day for 4 weeks.

The rats were examined throughout the study for any clinical and behavioral adverse effects caused by Nanogen's PEG-IFNλ1 administration. After the test period, the survived rats were sacrificed for autopsy and biochemical analyses. Blood samples were also collected from abdominal artery to conduct hematologic tests.

The test method and results are summarized in table 5.

TABLE 5

| Animals | Administration route | Administration period | Dose (mg/kg) | Volume (ml) |
|---|---|---|---|---|
| Rats 5 males, 5 females | Subcutaneous injection | Once a day for 4 weeks | 3<br>0.3<br>0.03 | 1.0 |
| Rats 5 males, 5 females | Intraperitoneal injection | Once a day for 4 weeks | 3<br>0.3<br>0.03 | 1.0 |

| Examination/Analysis | Male rats | Female rats |
|---|---|---|
| Clinical signs | none | none |
| Body weight | Normal | Normal |
| Food consumption | Normal | Normal |
| Water consumption | Normal | Normal |
| Urinalysis | Normal | Normal |
| Hematology | Normal | Normal |
| Urinalysis | Normal | Normal |
| Hematology | Normal | Normal |
| Serum biochemistry | Normal | Normal |
| Absolute and relative organ weight | Normal | Normal |
| Autopsy result | Normal | Normal |
| Histopathological examination | Normal | Normal |

There was no death in any groups during the entire study and no clinical signs were detected from the tested rats. The tested rats were normal in other examination categories and analyses even in the high dosage group. Therefore, the study shows that Nanogen's PEG-IFNλ1 does not have toxic effects in rats when it is administered repeatedly at the dosage of 3 mg/kg.

Immunological toxicity of PEG-IFNλ1: A study was carried out to investigate immunologic potential of Nanogen's PEG-IFNλ1 in guinea pigs. Healthy male Hartley guinea pigs with body weight of 300-500 gram were injected with PEG-IFNλ1 twice a week for 3 weeks either at a high dose (3 mg/kg) or low dose (0.03 mg/kg) and ovalbumin as control. Fourteen days after the final sensitization, the anaphylaxis test was performed by intravenously injecting a high dose of PEG-IFNλ1. The study included PEG-IFNλ1 incorporated in Freund's complete adjuvant (FCA). The sensitized guinea pigs were observed for active systemic anaphylaxis reactions after injection of a high dose PEG-IFNλ1. A list of indications was used as a sign of anaphylactic reaction and their occurrence was monitored in each tested animal.

Table 6 shows the study method and results.

TABLE 6

| Test groups | Dose | Administration route | Anaphylaxis challenge | No. of animals |
|---|---|---|---|---|
| Negative control (PBS) | — | Subcutaneous | Intravenous injection of PBS | 5 males |
| Positive control (ovalbumin) | 2 mg/kg | Subcutaneous | Intravenous injection of ovalbumin | 5 males |
| Low dose | 0.03 mg/kg | Subcutaneous | Intravenous injection of 3 mg/kg PEG-IFNλ1 | 5 males |
| High dose | 3 mg/kg | Subcutaneous | Intravenous injection of 3 mg/kg PEG-IFNλ1 | 5 males |
| High dose + FCA | 3 mg/kg + FCA | Subcutaneous | Intravenous injection of 3 mg/kg PEG-IFNλ1 | 5 males |

| Anaphylaxis challenge | Animal | Physical observation[1] | | | | | | | |
|---|---|---|---|---|---|---|---|---|---|
| | | 1 | 2 | 3 | 4 | 5 | 6 | 7 | 8 |
| PBS | 1 | – | – | – | – | + | – | – | – |
| | 2 | – | – | – | – | + | – | – | – |
| | 3 | – | – | – | – | + | – | – | – |
| | 4 | – | – | – | – | – | – | – | – |
| | 5 | – | – | – | – | + | – | – | – |
| OVALBUMIN (2 mg/kg) | 1 | – | + | + | – | + | + | + | + |
| | 2 | – | + | + | – | – | – | – | – |
| | 3 | – | + | + | + | + | + | + | + |
| | 4 | – | + | + | + | + | + | + | + |
| | 5 | – | + | + | + | – | – | – | – |
| Peg-IFNλ1 (0.03 mg/kg) | 1 | – | – | – | – | – | – | – | – |
| | 2 | – | – | – | – | + | – | – | – |
| | 3 | – | – | – | – | – | – | – | – |
| | 4 | – | – | – | – | + | – | – | – |
| | 5 | – | – | – | – | + | – | – | – |
| Peg-IFNλ1 (3 mg/kg) | 1 | – | – | – | – | + | – | – | – |
| | 2 | – | – | – | – | + | – | – | – |
| | 3 | – | – | – | – | + | – | – | – |
| | 4 | – | – | – | – | – | – | – | – |
| | 5 | – | – | – | – | + | – | – | – |
| Peg-IFNλ1 (3 mg/kg) + FCA | 1 | – | + | + | + | – | – | – | – |
| | 2 | – | +-- | +-- | – | + | – | – | – |
| | 3 | – | – | + | + | + | – | – | – |
| | 4 | – | + | + | – | + | – | – | – |
| | 5 | – | – | – | + | + | – | – | – |

[1] 1. Licking nose, rubbing nose; 2. Ruffling fur; 3. Labored breathing; 4. Sneezing, coughing; 5. Evacuation of feces, micturition; 6. Convulsion; 7. Prostration; 8. Death. –, negative; +, positive In the active systemic anaphylactic test, the guinea pigs slightly sensitized with high dose of PEG-IFNλ1 (3 mg/kg) incorporated in Freund's complete adjuvant (FCA) showed some indications of anaphylactic reaction. On the other hand, no guinea pigs sensitized with low dose and high dose of PEG-IFNλ1 (0.03 and 3 mg/kg) alone showed any anaphylactic reaction. No guinea pigs were dead after administration with Nanogen's PEG-IFNλ1 and negative treatment (PBS), but 3 pigs were dead after administration with ovalbumin (positive treatment). Therefore, it can be concluded that Nanogen's PEG-IFNλ1 does not induce systemic allergic reaction when administered alone in its clinical use.

It will be apparent to those skilled in the art that various modifications and variations can be made to the compounds, compositions, and methods of the present invention without departing from the spirit or scope of the invention. Thus, it is intended that the present invention cover the modifications and variations of this invention provided they come within the scope of the appended claims and their equivalents.

What is claimed:

1. A physiologically active PEG-IFNλ1 conjugate comprising the formula I:

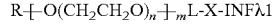

R—[—O(CH$_2$CH$_2$O)$_n$—]$_m$L-X-INFλ1    I wherein:

R is H or C$_{1-3}$ alkyl;

m is 1 or 2;

n is a positive integer selected in the range from 900-945;

L is selected from the group consisting of;

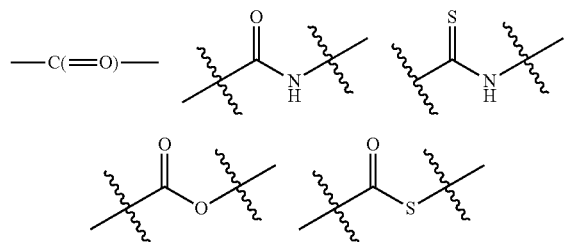

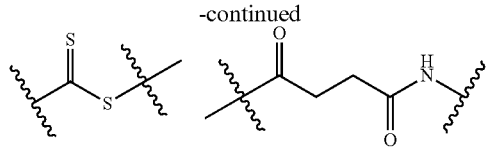

-continued

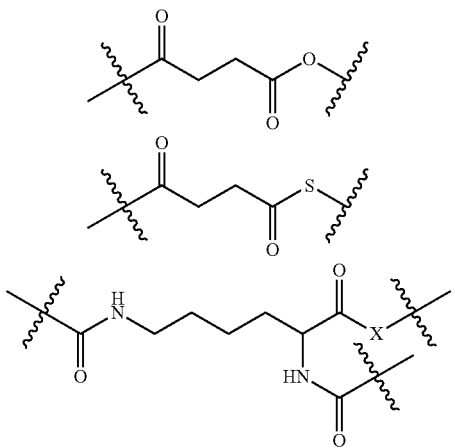

X is —O—, —NH— or —S—; and

IFNλ1 is interferon lambda 1 of SEQ ID No. 2;

or a pharmaceutically acceptable salt thereof.

2. The physiologically active PEG-IFNλ1 conjugate of claim 1 wherein:

R is $C_{1-3}$ alkyl;

m is 1 or 2;

n is a positive integer selected in the range from 900-945;

L is —C(=O)—;

X is —NH— or —S—; and

IFNλ1 is interferon lambda 1 of SEQ ID No. 2.

3. The conjugate of claim 1, where the conjugate has a blood serum half-life and persistence time that are prolonged or extended when compared to unconjugated IFNλ1.

4. The conjugate of claim 1, where the PEG is attached to the methionine at the N-terminus of the IFNλ1.

5. A pharmaceutical composition containing a conjugate according to claim 1 and pharmaceutically acceptable carriers and excipients.

6. A method of treating a patient infected or at risk of infection with a viral infection, comprising administering to a patient in need thereof, a therapeutically effective amount of the PEG-IFNλ1 conjugate of claim 1, a pharmaceutically acceptable salt thereof; or a pharmaceutical formulation thereof.

7. The method of claim 6, wherein the viral infection is caused by a hepatitis C virus or a hepatitis B virus, or the viral infection results in advance liver cirrhosis.

8. The method of claim 7, wherein the PEG-IFNλ1 is administered in a dose of about 0.5 μg/kg to 10.0 μg/kg weekly.

9. The method of claim 7, further comprising the administration of a nucleoside analogue selected from ribavirin and viramidine.

10. The method of claim 7, further comprising the administration of tenofovir.

11. A method of treating a patient infected or at risk of infection with a viral infection, comprising administering to a patient in need thereof, a therapeutically effective amount of a physiologically active PEG-IFNλ1 conjugate comprising the formula II:

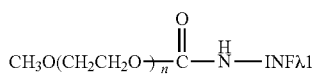

wherein INFλ1 is interferon lambda 1 of SEQ ID No: 2; and n is 900 to 945, a pharmaceutically acceptable salt thereof; or a pharmaceutical formulation thereof.

12. The method of claim 11, wherein the viral infection is caused by a hepatitis C virus or a hepatitis B virus, or the viral infection results in advance liver cirrhosis.

13. The method of claim 11, wherein the PEG-IFNλ1 is administered in a dose of about 0.5 μg/kg to 10.0 μg/kg weekly.

14. The method of claim 11, further comprising the administration of a nucleoside analogue selected from ribavirin and viramidine.

15. The method of claim 11, further comprising the administration of tenofovir.

* * * * *

SEQUENCE LISTING

<160> NUMBER OF SEQ ID NOS: 2

<210> SEQ ID NO 1
<211> LENGTH: 549
<212> TYPE: DNA
<213> ORGANISM: Artificial
<220> FEATURE:
<223> OTHER INFORMATION: DNA encoding interferon lambda 1

<400> SEQUENCE: 1

```
atgggccctg ttccgacctc taaacctacc accacgggta agggttgtca tattggtcgt      60
ttcaagtctc tgtccccgca ggaactggcc tctttcaaga aagctcgtga tgccctggaa     120
gagtctctga agctgaaaaa ctggagctgt tcttccccgg tgttcccggg caattgggac     180
ctgcgcctgc tgcaggttcg cgaacgcccg gtggctctgg aagctgagct ggctctgacc     240
ctgaaagtac tggaagcggc ggctggtccg gccctggaag acgttctgga tcagccgctg     300
cacaccctgc atcatattct gtcccagctg caggcttgca tccagcctca gccaaccgcc     360
ggtccgcgtc acgtggccg tctgcaccac tggctgcatc gcctgcagga agcgccgaaa     420
aaggagagcg ctggctgcct ggaagcaagc gtaaccttta acctgttccg tctgctgact     480
cgtgacctga aatatgttgc agatggcaat ctgtgcctgc gtacctccac ccacccggaa     540
tccacctga                                                              549
```

```
<210> SEQ ID NO 2
<211> LENGTH: 184
<212> TYPE: PRT
<213> ORGANISM: Artificial
<220> FEATURE:
<223> OTHER INFORMATION: Amino acid sequence of interferon lambda 1

<400> SEQUENCE: 2

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Ala
        35                  40                  45

Trp Ser Cys Ser Ser Pro Val Phe Pro Gly Asn Ala Trp Asp Leu Arg
    50                  55                  60

Leu Leu Gln Val Arg Glu Arg Pro Val Ala Leu Glu Ala Glu Leu Ala
65                  70                  75                  80

Leu Thr Leu Lys Val Leu Glu Ala Ala Ala Gly Pro Ala Leu Glu Asp
                85                  90                  95

Val Leu Asp Gln Pro Leu His Thr Leu His His Ile Leu Ser Gln Leu
            100                 105                 110

Gln Ala Cys Ile Gln Pro Gln Pro Thr Ala Gly Pro Arg Pro Arg Gly
        115                 120                 125

Leu His His Ala Trp Leu His Arg Leu Gln Glu Ala Pro Lys Lys Glu
    130                 135                 140

Ser Ala Gly Cys Leu Glu Ala Ser Val Thr Phe Asn Leu Phe Arg Leu
145                 150                 155                 160

Leu Thr Arg Asp Leu Lys Trp Val Ala Asp Gly Asn Leu Cys Leu Arg
                165                 170                 175

Thr Ser Thr His Pro Glu Ser Thr
            180
```